(12) United States Patent
Cutler et al.

(10) Patent No.: US 6,461,605 B1
(45) Date of Patent: Oct. 8, 2002

US006461605B1

(54) CONTINUOUS LOW-DOSE CYTOKINE INFUSION THERAPY

(75) Inventors: David L. Cutler, Morristown; Melton B. Affrime, Flemington, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/104,287

(22) Filed: Mar. 22, 2002

Related U.S. Application Data

(63) Continuation of application No. 09/311,767, filed on May 13, 1999, now abandoned, which is a continuation of application No. 08/742,305, filed on Nov. 1, 1996, now abandoned.
(60) Provisional application No. 60/006,130, filed on Nov. 2, 1995.

(51) Int. Cl.⁷ .................. A61K 38/21; A61K 45/00; A61K 38/00; A61K 39/29; A01N 25/00
(52) U.S. Cl. .............. 424/85.7; 424/85.1; 424/85.4; 424/228.1; 514/2; 514/12; 514/894; 435/811
(58) Field of Search ................ 424/85.1, 85.4, 424/85.7, 228.1; 514/2, 12, 894; 435/811

(56) References Cited

U.S. PATENT DOCUMENTS

| | | |
|---|---|---|
| RE29,835 E | 11/1978 | Witkowski et al. |
| 4,140,761 A | 2/1979 | Gerin et al. |
| 4,211,771 A | 7/1980 | Witkowski et al. |
| 4,530,901 A | 7/1985 | Weissmann |
| 4,791,192 A | 12/1988 | Nakagawa et al. |
| 4,985,253 A | 1/1991 | Fukioka et al. |
| 5,019,382 A | 5/1991 | Cummins et al. |
| 5,021,241 A | 6/1991 | Yamahira et al. |
| 5,026,687 A | 6/1991 | Yarchoan et al. |
| 5,122,614 A | 6/1992 | Zalipsky |
| 5,145,677 A | 9/1992 | Von Eihborn et al. |
| 5,279,833 A | 1/1994 | Rose et al. |
| 5,372,808 A | 12/1994 | Blatt et al. |
| 5,382,657 A | 1/1995 | Karasiewicz et al. |
| 5,539,063 A | 7/1996 | Hakimi et al. |
| 5,559,213 A | 9/1996 | Hakimi et al. |
| 5,580,859 A | 12/1996 | Felgner et al. |
| 5,595,732 A | 1/1997 | Hakimi et al. |
| 5,676,942 A | 10/1997 | Testa et al. |
| 5,767,097 A | 6/1998 | Tam |
| 5,849,800 A | 12/1998 | Smith |
| 6,177,074 B1 | 1/2001 | Glue et al. |
| 6,299,872 B1 | 10/2001 | Albrecht et al. |

FOREIGN PATENT DOCUMENTS

| | | |
|---|---|---|
| EP | 0 235 906 | 9/1987 |
| EP | 0 510 356 A1 | 10/1992 |
| EP | 0 707 855 A2 | 4/1996 |
| EP | 0 809 996 A2 | 12/1997 |
| EP | 0 593 868 A1 | 4/1998 |
| WO | WO 93/20835 | 10/1993 |
| WO | WO 93/21229 | 10/1993 |
| WO | WO 94/04179 | 3/1994 |
| WO | WO 94/14474 | 7/1994 |
| WO | WO 94/20131 | 9/1994 |
| WO | WO 95/13090 | 5/1995 |
| WO | WO 96/11953 | 4/1996 |
| WO | WO 96/36351 | 11/1996 |
| WO | WO 97/16204 | 5/1997 |
| WO | WO 97/18832 | 5/1997 |

OTHER PUBLICATIONS

Bizollon, et al., Revue Francaise De Castro–Enterologie, No. 297, vol. XXX, p. 429 (1994)(English & French Language Versions).
Bizollon, et al., J. Hepatol. 23(2):22–25 (1995).
Bodenheimer, et al., Hepatology 20(4):PT.2. Abstract No. 441(1994).
Braconier, et al., Scan. J. Infect. Dis., 27:325–329(1995).
Brillanti, et al., Hepatology 18:150A (Abstract No. 375) (1993).
Brillanti, et al. J. Hepatol. 18 (Suppl.1):S101 (Abstract No. T–69).
Brillanti, et al., Gastroenterology 107:812–817 (1994).
Brillanti, et al., J. Hepatol., 23(Suppl. 2):13–16 (1995).
Brouwer, et al., J. Hepatol. 21(Suppl. 1):S17(Abstract No. WP2/08) (1994).
Carreno, et al., Journal of Medical Virology 37:215–219 (1992).
Cavailetto, et al., Ital. J. Gastrenterol, vol. 25, Congress Proceedings (Venezia, Nov. 11–13, 1993) pp. 443–468 (Abstract at p. 452).
Chemello, et al., J. Hepatol 21(Suppl. 1):S12 (Abstract GS 5/29) (1994).
Chemello, et al., J. Hepatol., 23(Suppl. 2):8–12 (1995).
Coltrill, et al., Clinical Oncology, 9:365–380 (1997).
Davis, et al., N. Engl. J. Med., 339:1493–1492–1499 (1998).
Di Bisceglie, et al., Hepatology 16:649–654 (1992).
Dorr, et al., Journal of Interferon Research 8:717–725 (1988).
Fuertges, et al., Journal of Controlled Release 11:139–148 (1990).
Hakozaki, et al., Am. J. Gastroenterology 90(8):1246–1249 (1995).

(List continued on next page.)

*Primary Examiner*—Gary L. Kunz
*Assistant Examiner*—Jegatheesan Seharaseyon
(74) *Attorney, Agent, or Firm*—Lerner, David, Littenberg, Krumholz & Mentlik, LLP

(57) ABSTRACT

A method is provided for treating conditions that are susceptible of treatment with a cytokine wherein the undesirable side effects normally associated with cytokine administration are diminished or eliminated. The method comprises continuously administering a low dose of a cytokine to an individual afflicted with a condition susceptible of treatment with the cytokine. In a preferred embodiment of the invention, chronic hepatitis C is treated by administering a low dose amount of interferon.

14 Claims, No Drawings

OTHER PUBLICATIONS

Hoofnagle, et al., New Eng. J. Med. 315:1575–1578 (1986).
Inada, et al., TIBTECH 13:86–91 (1995).
Jacyna, et al., British Medical Journal 298:80–82 (1989).
Kakumu, et al., Gastroenterology 105:507–512 (1993).
Lai, et al., Hepatology 18:93A (Abstract No. 146) (1993).
Ludwig, et al., Proc. Am. Soc. Clin. Oncol. 5:234 Abstract No. 915 (1986).
Main, J. Hepatol 23(Suppl. 2):32–36 (1995).
Marcellin, et al., Baillere's Clin. Gastroenter. 8:233–253 (1994).
McHutchison, et al., N. Engl. J. Med., 339:1485–1492 (1998).
The Merck Index, 11$^{th}$ Ed., Compound No. 8199 p. 1304 (1989).
Nieforth, et al., Clin. Pharmacol. Ther., 59:636–646 (1996).
Northfelt, et al., Journal of Acquired Immune Deficiency Syndromes and Human Retrovirology 8:45–50 (1995).
Northfelt, et al., Am. J. Hematology 38:238 (1991).
Nucci, et al., Advanced Drug Delivery Reviews 6:133–151 (1991).
Poynard, et al., Lancet 352:1426–1432 (1998).
Reichard, et al, J. Hepatol 26(Suppl.1):1085–111S(1997).
Reichard, et al., Lancet 351:83–87 (1998).
Reichen, et al., Clin. Invest. 71:888 (1993).
Sambataro, J. Hepatol., 18(Suppl. 1): S167 (Abstract No. T–377) (1993).
Schvarcz, et al., J. Med. Virol. 46:43–47 (1995).
Schvarcz, et al., J. Hepatol., 23(Suppl. 2):17–21 (1995).
Sherlock, S. Hepatol 23(Suppl. 2):1–2 (1995).
Sherlock, S. Hepatol. 23(Suppl. 2):3–7 (1995).
Smith, et al., J. Hepatol., 23(Suppl. 2):26–31 (1995).
Telfer, et al., British J. Haemtatology 98:850–855 (1997).
Thomas, et al., Hepatology, vol. 20, No. 4, Pt. 2, Abstract No. 440 (1994).
Trepo, et al. Antiviral Res., 24:155–163 (1994).
Wu, et al., Antiviral Res. (Suppl. 1) Abstract No. 228 (1993).
Panel Discussion, J. Hepatol 23(Suppl. 2):37–40 (1995).
Package Insert for Intron A Interferon Alpha–2b Recombinant, 1992, Schering Corporation, Kenilworth, NJ.
Orkin, et al., Report and Recommendation of the Panel to Assess the NIH Investment in Research on Gene Therapy. NIH publication. (1995).
Reichard et al., Hepatology, 19:280–285 (1994).
Ludwig, Schweiz. Med. Wochenschr. 119(44):1539–44 (1989).
Lai, et al., Symposium to the 9$^{th}$ Biennial Scientific Mtg., Asian Pacific Assoc. for the Study of the Liver (1994).
Lai, et al., Gastroenterology 111:1307–1312 (1996).
Liang, et al., N. Engl. J. Med. 339:1549–1550 (1998).

CONTINUOUS LOW-DOSE CYTOKINE INFUSION THERAPY

This application is a continuation of U.S. patent application Ser. No. 09/311,767, filed May 13, 1999 (abandoned), which is a continuation of U.S. patent application Ser. No. 08/742,305, filed Nov. 1, 1996, abandoned, which claims the benefit of provisional patent application No. 60/006,130, filed Nov. 2, 1995, disclosures of which are hereby incorporated by reference in their entireties.

FIELD OF THE INVENTION

The invention relates to a method of treating medical conditions, in particular viral infections, that are susceptible to treatment with a cytokine comprising the continuous administration of a low dose of the cytokine. In a preferred embodiment of the invention, continuous low-dose infusion of interferon is used to treat chronic hepatitis C.

BACKGROUND OF THE INVENTION

Interferons are a family of naturally occurring small proteins and glycoproteins produced and secreted by most nucleated cells in response to viral infection as well as other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events. In vitro studies demonstrated that these include the induction of certain enzymes, suppression of cell proliferation, immunomodulating activities such as enhancement of the phagocytic activity of macrophages and augmentation of the specific cytotoxicity of lymphocytes for target cells, and inhibition of virus replication in virus-infected cells.

Nonimmune interferons, which include both alpha and beta interferons, are known to suppress human immunodeficiency virus (HIV) in both acutely and chronically infected cells. Poli and Fauci, 1992, *AIDS Research and Human Retroviruses* 8(2):191–197. Interferons, in particular, alpha interferons, have received considerable attention as therapeutic agents in the treatment of hepatitis C virus (HCV)-related disease due to their antiviral activity. Hoofnagle et al., in: *Viral Hepatitis 1981 International Symposium*, 1982, Philadelphia, Franklin Institute Press; Hoofnagle et al, 1986, *New Eng. J Med.* 315:1575–1578; Thomson, 1987, *Lancet* 1:539–541 Kiyosawa et al., 1983, in: Zuckerman, ed., *Viral Hepatitis and Liver Disease*, Allen K. Liss, New York pp. 895–897; Hoofnagle et al., 1985, *Sem. Liv. Dis.*, 1985, 9:259–263.

Chronic hepatitis C is an insidious and slowly progressive disease having a significant impact on the quality of life. Despite improvement in the quality of the blood-donor pool and the recent implementation of testing of donated blood for HCV, the estimated incidence of acute infection among persons receiving transfusions is 5 to 10%. Alter et al., in: Zuckerman, ed., *Viral Hepatitis and Liver Disease*, Allen K. Liss, New York, 1988, pp. 537–542. Thus, of the approximately 3 million persons who receive transfusions in the United States each year, acute hepatitis C will develop in about 150,000. While many patients who contract hepatitis C will have subclinical or mild disease, approximately 50% will progress to a chronic disease state characterized by fluctuating serum transaminase abnormalities and inflammatory lesions on liver biopsy. It is estimated that cirrhosis will develop in up to about 20% of this group. Koretz et al., 1985, *Gastroenterology* 88:1251–1254.

Interferons are known to affect a variety of cellular functions, including DNA replication and RNA and protein synthesis, in both normal and abnormal cells. Thus, cytotoxic effects of interferon are not restricted to tumor or virus infected cells but are also manifested in normal, healthy cells as well. As a result, undesirable side effects arise during interferon therapy, particularly when high doses are required. Administration of interferon can lead to myelosuppression resulting in reduced red blood cell, white blood cell and platelet levels. Higher doses of interferon commonly give rise to flu-like symptoms (e.g., fever, fatigue, headaches and chills), gastrointestinal disorders (e.g., anorexia, nausea and diarrhea), dizziness and coughing.

Interferon alpha-2b has been shown to be safe and effective when administered subcutaneously at a dose of $3 \times 1 Q6$ international units (IU) three times a week for 24 weeks for the treatment of chronic hepatitis C. Causse et al., 1991, *Gastroenterology* 101:497–502; Davis et al., 1989, *New Eng. J Med.* 321:1501–1506; Marcellin et al., 1991, *Hepatology*, 13(3):393–393. This amount and duration alleviates symptoms of hepatitis C and biochemical or histological evidence of ongoing inflammation of the liver in some patients but it also causes undesirable side effects, e.g., flu-like symptoms. While Carreno et al. (*Journal of Medical Virology*, 1992, 37:215–219) reported treatment of patients with chronic hepatitis C with a daily dose of $9 \times 106$ IU Roferon® A administered for 28 days by continuous subcutaneous infusion to patients with chronic hepatitis C, all twelve of the patients treated had flu-like symptoms and fever. During the first week of treatment 8 patients experienced headache and arthralgias. Eight patients had some hair loss, 9 patients suffered weight loss of between 2–5 kg, and 11 patients had decreases in platelet and leukocyte counts. While significant decreases in serum ALT levels were reported, HCV RNA remained positive during the treatment period.

Continuous infusion of interferon has also been used in the treatment of cancer patients. See Dorr et al., 1988, *Journal of Interferon Research* 8:717–725, which reports continuous 28-day subcutaneous infusion of Roferon®A at doses of from $0.7 \times 106$ to $5.0 \times 106$ $IU/in^2$ body surface area and Ludwig et al., 1986, *Proc. Am. Soc. Clin. Oncol.* 5:234, Abstr. 915, which reports continuous subcutaneous infusion of $3–18 \times 106$ IU/day of Roferon®A for periods of more than 3 months.

Undesirable side effects, such as those accompanying interferon therapy, also occur in treatment protocols employing other cytokines. Such side effects frequently limit the therapeutic usefulness of such agents. Thus, a need exists to reduce or eliminate the undesirable side effects of cytokine therapy without diminishing the therapeutic benefits of such therapy.

SUMMARY OF THE INVENTION

The present invention fulfills this need by providing a method of treating conditions that are susceptible of treatment with a cytokine, wherein undesirable side effects normally associated with such treatments are significantly diminished or eliminated entirely.

An object of the invention is to provide a method of treating a mammal afflicted with a condition that is susceptible to treatment with a cytokine comprising administering to a mammal in need of cytokine therapy a low-dosage amount of a cytokine by continuous infusion of the cytokine.

Another object of the invention is to treat viral infections comprising continuously administering a low dosage amount of a cytokine to a mammalian host infected with a virus susceptible to treatment by the cytokine.

Yet another object of the invention is directed to a method of treating chronic hepatitis C virus infection comprising continuously administering to a mammalian host infected with hepatitis C virus a low dosage amount of interferon, preferably alpha interferon, more preferably interferon alpha-2b.

DETAILED DESCRIPTION OF THE INVENTION

All references cited herein are incorporated in their entirety by reference. The invention is directed to a method of treating conditions that are susceptible of treatment with a cytokine. It has been unexpectedly discovered that continuous administration of low doses of cytokines over a prolonged period of time provides effective therapeutic benefits, while significantly diminishing the undesirable side effects normally associated with conventionally practiced cytokine treatment regimes.

Conditions that can be treated in accordance with the present invention are generally those that are susceptible to cytokine treatment. Cytokine-susceptible conditions include conditions which would respond positively or favorably as these terms are known in the medical arts to cytokine based therapy. For purposes of the invention, conditions that can be treated with cytokine therapy include those conditions in which treatment with a cytokine shows some efficacy, but which may not be treatable with the cytokine because the negative side effects outweigh the benefits of the treatment. For example, side effects accompanying alpha interferon therapy have virtually ruled out treatment of Epstein Barr virus using alpha interferon. Practice of the invention results in substantially reduced or eliminated side effects as compared to conventional interferon treatment.

Cytokines which can be used to practice the invention include but are not limited to interferons, granulocyte colony stimulating factor (G-CSF), granulocyte/macrophage colony stimulating factor (GM-CSF), tumor necrosis factor (TNF), erythropoietin, thrombopoietin and interleukins. In addition, other therapeutic agents, such as antibodies and fragments thereof (e.g., Fab fragments), soluble cytokine receptors and cytokine receptor antagonists can advantageously be administered in accordance with the practice of the invention.

Cytokines can be used alone or in combination with other cytokines and/or therapeutic agents. For example, interferon can be used alone or in combination with AZT in the treatment of HIV/AIDS or in combination with ribivirin in the treatment of HCV.

While the invention will hereinafter be described in terms of the use of interferon, it is to be understood that the administration of other cytokines, alone or in combination with one or more other therapeutic agents, is encompassed by the invention.

The term "interferon" as used herein means the family of highly homologous species-specific proteins that inhibit viral replication and cellular proliferation and modulate immune response. Human interferons are grouped into three classes based on their cellular, origin and antigenicity: α-interferon (leukocytes), β-interferon (fibroblasts) and γ-interferon (T cells). Recombinant forms of each group have been developed and are commercially available. Subtypes in each group are based on antigenic/structural characteristics. At least 14 α-interferons (grouped into subtypes A through H) having distinct amino acid sequences have been identified by isolating and sequencing DNA encoding these peptides. Both naturally occurring and recombinant α-, β- and γ-interferons, including consensus interferon, may be used in the practice of the invention.

The purification of interferon from human leukocytes isolated from the buffy coat fraction of whole blood is described in U.S. Pat. No. 4,503,035. Human leukocyte interferon prepared in this manner contains a mixture of different human leukocyte interferon amino acid sequences. Purified natural human a-interferons and mixtures thereof which may be used in the practice of, the invention include but are not limited to Sumiferon® interferon alfa-n1 available from Sumitomo, Japan, Wellferon® interferon alfa-n1 (Ins) available from Glaxo-Wellcome Ltd., London, Great Britain, and Alferon® interferon alfa-n3 available from the Purdue Frederick Co., Norwalk, Conn.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains its in vitro and in vivo antiviral and immunomodulatory activities. It is also understood that the recombinant techniques could also include a glycosylation site for addition of a carbohydrate moiety on the recombinantly-derived polypeptide.

The construction of recombinant DNA plasmids containing sequences encoding at least part of human leukocyte interferon and the expression in *E. coli* of a polypeptide having immunological or biological activity of human leukocyte interferon is disclosed in U.S. Pat. No. 4,530,901. The construction of hybrid α-interferon genes containing combinations of different subtype sequences (e.g., A and D, A and B, A and F) is disclosed in U.S. Pat. Nos. 4,414,150, 4,456,748 and 4,678,751. Typical suitable recombinant α-interferons which may be used in the practice of the invention include but are not limited to interferon alfa-2b such as Intron® A available from Schering Corporation, Kenilworth, N.J., interferon alfa-2a such as Roferon® A available from Hoffmann-La Roche, Nutley, N.J. and interferon alfa-2c such as Berofor® available from Boehringer Ingelheim Pharmaceutical, Inc., Ridgefield, Conn. U.S. Pat. Nos. 4,695,623 and 4,897,471 disclose human leukocyte interferon polypeptides, referred to as consensus interferon, which have amino acid sequences which include common or predominant amino acids found in each position among naturally-occurring alpha interferon subtype polypeptides. Consensus interferon which may also be used in the practice of the invention is available from Amgen, Inc., Newbury Park, Calif.

Suitable β-interferons which may be used to practice the invention include but are not limited to Betaseron® interferon beta-1b, a synthetic mutein having a serine substituted for the cysteine residue at position 171 of the native molecule, available from Berlex Laboratories, Richmond, Calif. Suitable γ-interferons which may be used to practice the invention include but are not limited to Actimmune® recombinant interferon gamma-ib available from Genentech, South San Francisco, Calif.

Exemplary conditions which can be treated with interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with interferon may be used to treat conditions which would benefit from inhibiting the replication of interferon-sensitive viruses. Viral infections which may be treated in accordance with the invention include hepatitis A, hepatitis B, hepatitis C, other non-A/non-B hepatitis, herpes virus (Epstein-Barr virus (EBV), cytomegalovirus (CMV), herpes simplex, human herpes virus type 6 (HHV-6)), papilloma, poxvirus, picornavirus, adenovirus, rhinovirus, human T-lymphotropic virus-type 1 and 2 (HTLV-1/2), human rotavirus, rabies, retroviruses including human immunodeficiency virus (HIV), encephalitis and respiratory viral infections. The method of the invention can also be used to modify various immune responses.

Two variants of a-interferon are currently approved in the United States and other countries for the treatment of hairy cell leukemia, venereal warts, Kaposi's Sarcoma, and chronic non-A/non-B hepatitis: interferon alfa-2b, marketed under the trade name INTRON® A (Schering Corporation, Kenilworth N.J.) and interferon alfa-2a, marketed under the trade name Roferon® A (Hoffmann-La Roche, Nutley, N.J.). Since interferon alpha-2b, among all interferons, has the broadest approval throughout the world for treating chronic hepatitis C infection, it is most preferred for use in the treatment of chronic hepatitis C in accordance with practice of the invention.

A person suffering from chronic hepatitis C infection may exhibit one or more of the following signs or symptoms: (a) elevated ALT, (b) positive test for anti-HCV antibodies, (c) presence of HCV as demonstrated by a positive test for HCV-RNA, (d) clinical stigmata of chronic liver disease, (e) hepatocellular damage. Such criteria may not only be used to diagnose hepatitis C, but can be used to evaluate a patient's response to drug treatment.

Elevated serum alanine aminotransferase (ALT) and aspartate aminotransferase (AST) are known to occur in uncontrolled hepatitis C, and a complete response to treatment is generally defined as the normalization of these serum enzymes, particularly ALT (Davis et al., 1989, New Eng. J. Med. 321:1501–1506). ALT is an enzyme released when liver cells are destroyed and is symptomatic of HCV infection. Interferon causes synthesis of the enzyme 2',5'-oligoadenylate synthetase (2'5'OAS), which in turn, results in the degradation of the viral mRNA. Houglum, 1983, Clinical Pharmacology 2:20–28. Increases in serum levels of the 2'5'OAS coincide with decrease in ALT levels.

In order to follow the course of HCV replication in subjects in response to drug treatment, HCV RNA may be measured in serum samples by, for example, a nested polymerase chain reaction assay that uses two sets of primers derived from the N53 and N54 non-structural gene regions of the HCV genome. Farci et al., 1991, New Eng. J. Med. 325:98–104. Ulrich et al., 1990, J. Clin. Invest., 86:1609–1614.

Histological examination of liver biopsy samples may be used as a second criteria for evaluation. See, e.g., Knodell et al., 1981, Hepatology 1:431–435, whose Histological Activity Index (portal inflammation, piecemeal or bridging necrosis, lobular injury and fibrosis) provides a scoring method for disease activity.

In the practice of the invention, a low dose of interferon is continuously administered to a mammal, in particular a human patient, exhibiting one of more of the above signs or symptoms in an amount and for a period of time sufficient to eliminate or at least alleviate one or more of the above-mentioned signs or symptoms.

As used herein, a low dose is an amount which for a given period of time is less than or equal to amounts used in traditional bolus or intermittent therapies over such a time period. The terms "continuous administration" and "continuous infusion" are used interchangeably herein and mean maintaining a steady state serum level of interferon throughout the course of the treatment period. This can be accomplished by constantly or repeatedly injecting substantially identical amounts of interferon, e.g., at least every hour, 24 hours a day, seven days a week, such that a steady state serum level is achieved for the duration of treatment.

Continuous low dose interferon administration may be by subcutaneous or intravenous injection at appropriate intervals, e.g. at least hourly, for an appropriate period of time in an amount which will facilitate or promote in vivo inactivation of hepatitis C virus.

Continuous subcutaneous administration can by accomplished by, for example, a pulsatile electronic syringe driver (Provider Model PA 3000, Pancretec Inc., San Diego Calif.), a portable syringe pump such as the Graseby model MS 1 6A (Graseby Medical Ltd., Watford, Herts England), or a constant infusion pump such as the Disetronic Model Panomat C-S. Osmotic pumps, such as that available from Alza, may also be used. Since use of continuous subcutaneous injections allows the patient to be ambulatory, it is preferred over use of continuous intravenous injections.

Formulations which simulate a constant low dose injection, such as but not limited to long-acting cytokine-polymer conjugates and various-sustained release formulations, are also contemplated for use.

Cytokine conjugates can be prepared by coupling a cytokine, such as interferon, to a water-soluble polymer. A non-limiting list of such polymers include polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917,888, European Patent Application No. 0 236 987, European Patent Application No. 0 510 356 and International Application Publication No. WO 95/13090. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced.

Various extended or sustained-release formulations can be prepared using conventional methods well known in the art.

Constant low dose administration may also be accomplished by gene therapy, e.g., by administering an interferon retroviral or other vector so as to produce interferon in vivo.

In general, components of interferon compositions can be selected from among those commonly employed with interferons and other antiproliferative or antiviral agents and which are known to those skilled in the art. Conventional pharmaceutical compositions comprising a therapeutically effective amount of interferon together with pharmaceutically acceptable carriers, adjuvants, diluents, preservatives and/or solubilizers may be used in the practice of the invention, Pharmaceutical compositions of interferon include diluents of various buffers (e.g., Tris-HCl, acetate, phosphate) having a range of pH and ionic strength, carriers (e.g., human serum albumin), solubilizers (e.g., tween, polysorbate), and preservatives (e.g., thimerosol, benzyl alcohol). Pharmaceutical composition of interferon are commercially available as injectable solutions and as lyophilized powders which are reconstituted in an appropriate diluent prior to injection.

Duration of treatment is at least 4 weeks, preferably 12 weeks or longer. For treatment of chronic HCV in accordance with the practice of the invention, a total weekly dose of alpha interferon-2b should range from 2 to 10 million IU, more preferable, 5–10 million IU, most preferably 8–10 million IU per week.

While administration or infusion is to be continuous, frequency of injection of the interferon composition will depend on the form of the composition. It will be understood that injection will be less frequent (e.g., once or twice a week) when using sustained release formulations or long-acting polymer conjugates. A single injection may be sufficient when using viral vectors to express the cytokine in vivo.

As described above, the course of the disease and its response to drug treatments may be followed by clinical examination and laboratory findings. The effectiveness of the therapy of the invention is determined by the extent to which the previously described signs and symptoms of chronic hepatitis are alleviated and the extent to which the normal side effects of interferon (i.e., flu-like symptoms such as fever, headache, chills, myalgia, fatigue, etc. and central nervous system related symptoms such as depression, paresthesia, impaired concentration, etc.) are eliminated or substantially reduced.

The invention can be illustrated by the following non-limiting example.

EXAMPLE

Seven human patients with chronic hepatitis C were treated in accordance with the invention.

Human subjects selected for treatment were chosen from anti-HCV antibody positive patients with biopsy documented chronic active hepatitis. Each patient was positive for antibody to hepatitis C virus (anti-HCV) by supplemental assay (Ortho or Abbott) and had previous liver biopsy with features of chronic hepatitis.

Each patient treated in accordance with the invention had previously undergone a 24 week course of INTRON® A administered by subcutaneous injection, $3 \times 10^6$ IU three times a week with complete response (defined as normalization of ALT), followed by relapse of chronic hepatitis C (loss of ALT response).

All patients were treated for 12 weeks with a low-dose subcutaneous infusion of INTRONG® A. INTRON® A was administered at a concentration of $5 \times 10^6$ IU/mi at an infusion rate of 0.012 ml/hr into the subcutaneous tissue of the anterior abdominal wall by continuous subcutaneous infusion using a constant infusion pump (Disetronic Model Panomat C-5). Thus, INTRON® A was continuously administered at a daily rate of $1.4 \times 1~10^6$ IU/day ($60 \times 10^3$ IU/hr), or approximately $10 \times 10^6$ IU/week.

Patients were monitored weekly for clinical symptoms, pharmacodynamics (serum $\beta_2$-microglobulin, 2'5'OAS, serum IFNα-2b concentration) and antiviral response (ALT normalization, disappearance of hepatitis C RNA (HCV-RNA) by immunoassay and polymerase chain reaction).

Therapy was well tolerated. Adverse events were mild and consisted primarily of fatigue. All patients had a 50% or greater decrease in ALT. Four patients had persistent normalization of ALT during therapy. $B_2$ microglobulin and 2'5'OAS concentrations remained elevated above baseline throughout treatment without indication of down-regulation of response. HCV RNA by immunoassay became negative in all patients, with a mean time to response of 4 weeks. Mean serum IFNα-2b concentrations were detectable, but were less than the limit of quantification of the assay (10 IU/mi).

This example shows that constant low concentrations of IFNα-2b are effective in normalizing ALT and suppressing HCV replication. No evidence of down-regulation of pharmacodynamic response was observed.

While the results were transient in that the markers return upon cessation of therapy, longer treatment is expected to result in clinical improvements based on normal transaminase levels and further treatment to cure (normal liver histology) even on removal of treatment.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a hepatitis C viral infection in a human comprising continuously parenterally administering interferon alpha to the human in an amount from about 2 million IU per week to about 10 million IU per week.

2. The method of claim 1 wherein said continuous administration is conducted subcutaneously.

3. The method of claim 1 wherein said continuous administration is conducted by injection of a sustained-release formulation of the interferon alpha.

4. The method of claim 1 wherein said continuous administration is accomplished by injection of a polymer-interferon alpha conjugate.

5. The method of claim 4 wherein the polymer is polyethylene glycol.

6. The method of claim 1 wherein the interferon alpha is interferon alpha-2b.

7. The method of any one of claims 1, 2, 3, 4, 5 or 6 wherein the interferon alpha is used in combination with ribavirin.

8. The method of claim 1 wherein the interferon alpha is used in combination with at least one other cytokine selected from the group consisting of G-CSF, GM-CSF, IL-1, IL-3, IL-6 and erythropoietin.

9. The method of claim 1 wherein said amount is about 2 million IU interferon alpha per week.

10. The method of claim 1 wherein said amount is from about 2 to 5 million IU interferon alpha per week.

11. The method of claim 1 wherein said amount is from about 2 to 8 million IU interferon alpha per week.

12. The method of claim 1 wherein said amount is from 5 to 8 million IU interferon alpha per week.

13. The method of claim 1 wherein said amount is 5 million IU interferon alpha per week.

14. The method of claim 1 wherein said amount is 8 million IU interferon alpha per week.

* * * * *

UNITED STATES PATENT AND TRADEMARK OFFICE
CERTIFICATE OF CORRECTION

PATENT NO.   : 6,461,605 B1  Page 1 of 1
DATED        : October 8, 2002
INVENTOR(S)  : David L. Cutler and Melton B. Affrime It is certified that error appears in the above-identified patent and that said Letters Patent is hereby corrected as shown below:

<u>Column 5,</u>
Line 62, "of" should read -- or --.

<u>Column 7,</u>
Line 50, "INTRONG" should read -- INTRON --.

Signed and Sealed this

Twenty-fifth Day of February, 2003

JAMES E. ROGAN
*Director of the United States Patent and Trademark Office*